United States Patent [19]
Ando

[11] Patent Number: 4,486,103
[45] Date of Patent: Dec. 4, 1984

[54] METHOD OF AND SYSTEM FOR INSPECTING PERFORMANCE OF HEAT-INSULATING LAYER SURROUNDING A PIPE

[75] Inventor: Masao Ando, Yokohamashi, Japan
[73] Assignee: Chisso Corporation, Tokyo, Japan
[21] Appl. No.: 421,248
[22] Filed: Sep. 22, 1982
[30] Foreign Application Priority Data
  Sep. 25, 1981 [JP] Japan .................. 56-151631
[51] Int. Cl.³ .................................. G01N 25/72
[52] U.S. Cl. ........................................ 374/5; 374/4
[58] Field of Search ........... 374/4, 5, 43, 44, 57, 374/147, 29; 250/342, 340, 316.1

[56] References Cited
U.S. PATENT DOCUMENTS

| | | | |
|---|---|---|---|
| 1,869,336 | 7/1932 | De Forest | 374/4 |
| 3,864,958 | 2/1975 | Dreitzler et al. | 374/4 |
| 3,911,727 | 10/1975 | Katsuta et al. | 374/4 |
| 4,034,286 | 7/1977 | Lev et al. | 374/4 |

FOREIGN PATENT DOCUMENTS
2055192  5/1972  Fed. Rep. of Germany .......... 374/4

Primary Examiner—Charles Frankfort
Assistant Examiner—David R. Schuster
Attorney, Agent, or Firm—Fred Philpitt

[57] ABSTRACT

A method of inspecting heat-insulation performance of a heat-insulating layer surrounding a pipe, which method comprises inserting an insulated electrical conductor line in the pipe having a heat-insulating layer therearound, in case where the pipe is a metal pipe, or another metal pipe laid along the pipe and placed in the inside of the heat insulating layer; causing an AC current flow through the conductor line to thereby induce a secondary current which flows through the pipe or another metal pipe; and measuring the temperature of various points of the outer surface of the heat-insulating layer by a non-contact thermometer to thereby determine the variance of the heat-insulation performance of the heat-insulating layer in terms of the variance of temperature thereof.

7 Claims, 3 Drawing Figures

METHOD OF AND SYSTEM FOR INSPECTING PERFORMANCE OF HEAT-INSULATING LAYER SURROUNDING A PIPE

BACKGROUND OF THE INVENTION (1) Field of the Invention

This invention relates to a method of and a system for inspecting performance (or capacity) of heat-insulation of a pipeline unit having a heat-insulating layer for the purpose of temperature maintenance.

(2) Description of the Prior Art

A pipeline for transporting a cooling medium having temperature lower than ambient temperature, or a higher temperature fluid such as steam, fuel heavy oil or the like is usually provided with a heat-insulating material for the purpose of maintaining cold or hot temperature, such as foamed polyurethane, as the outer layer thereof, and units of these pipelines are prefabricated in a workshop and in a length of, for example, 10 to 15 m as a usual standard length of transportation steel pipes.

In such a case, an insulating material of polyurethane is foamed in a gap having a necessary thickness between a transportation steel pipe and a polyethylene or spiral steel pipe for protecting polyurethane. In order to form a polyurethane foamed layer having no unfilled part in the above-mentioned gap on this occasion, a raw material liquid of polyurethane in an amount slightly greater than the necessary amount is usually poured in the above-mentioned gap. However, even by such an arrangement, it is often experienced on actual working spots that polyurethane non-uniformly foams to create locally unfilled part, resulting in non-uniform insulating effect and trouble in the operation of the fluid transportation pipe. Such non-uniformity of insulating effect is experienced not only at the time of polyurethane foaming but also in the use of other shaped insulating material.

Accordingly, it has been necessary to inspect non-uniformity of the above-mentioned insulating layer but there has been no effective method. For example, there has been adopted such a method as the one in which internal foaming is observed by naked eyes by using, as a cover on the insulating material, a polyurethane sheet which is as thin as possible and nearly transparent, or another in which some samples are taken out from prefabricated unit pipes and cut to inspect the foaming state. However, both the methods have not been perfect. It may also be considered to inspect the whole surface of all the unit pipes by way of X-ray but since operation of X-ray apparatus needs special attention, technique and installation, this idea is not practical particularly for long distance pipelines.

SUMMARY OF THE INVENTION

It is an object of the present invention to provide a method for inspecting the performance of a heat-insulating layer surrounding the outer wall of a pipeline in a convenient way without breaking the once prefabricated insulating layer even when the cover on the insulating layer is opaque.

It is another object of the present invention to provide a system for inspecting the performance of a heat-insulating layer surrounding the outer wall of a pipeline in a convenient way without breaking the once prefabricated insulating layer.

The objects of the present invention can be attained by the method of the present invention.

The method of the present invention resides in:

a method of inspecting the heat-insulation performance of a heat-insulating layer surrounding the outer wall of a pipe, which method comprises inserting an insulated conducter line in the inside of said pipe in the case where said pipe is a metal pipe or in the interior of another metal pipe laid along said metal pipe and situated in the inside of said insulating layer, and holding it in said pipe or said another pipe during the time of inspection;

letting an AC current flow through said conductor line to induce a secondary induction current in said metal pipe or in said another metal pipe; and after causing the effect of the temperature elevation to appear on the outer surface of said heat-insulating layer, measuring the temperature of a part or the whole of the outer surface of said heat-insulating layer, by means of a non-contact thermometer, to determine the variance of measured temperatures to represent variance of heat-insulation performance, of said heat-insulating layer.

DETAILED DESCRIPTION OF THE INVENTION

Figure 1:
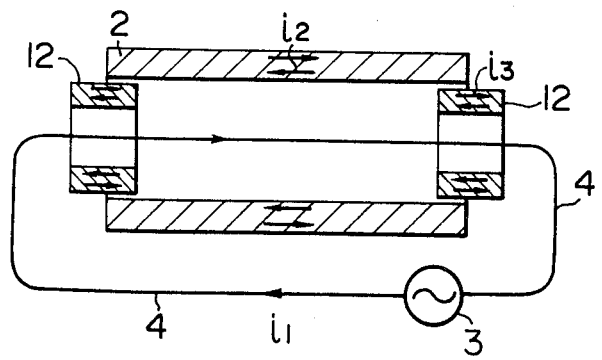
FIG. 1 is a schematic view illustrating the principle of fundamental heat-generating circuits (primary and secondary) in section, which are used in the method of the present invention for inspecting the performance of a heat-insulating layer surrounding a pipe.

According to the method of the present invention, when a material of fluid-transporting pipe is of an electrically conductive metal such as steel, said pipe generates heat by a secondary induced current $i_2$ flowing therethrough by placing an insulated conductor line through said fluid-transporting pipe and connecting said conductor line to an AC source so as to cause a primary current $i_1$ to flow through said conductor line as a primary circuit.

When the thickness t (cm) of the fluid-transporting pipe is sufficiently large, the range of flow of the secondary induction current within the transporting pipe is, as is well known, approximately the so-called skin depth of alternating current, S (cm). This S is shown by the following formula (1)

$$S = 5030 \sqrt{\frac{\rho}{\mu f}} \tag{1}$$

wherein $\rho$ ($\Omega$ cm) is an electric resistivity of the fluid-transporting pipe, $\mu$ is a specific permeability of the material thereof, and f is the frequency (Hz) of the alternating current.

In the range where the thickness of said fluid-transporting pipe satisfies the relation of $$t \geq 2S \qquad (2),$$

since a closed circuit is formed, the current $i_2$ flowing through a secondary induction circuit becomes almost constant, resulting in the relation of $i_1 = i_2$, and the heat generation per unit surface area of the fluid transporting pipe becomes also constant.

This generated heat not only heats the fluid-transporting pipe itself but also passes through a heat-insulating layer surrounding the fluid-transporting pipe with lapse of time, and balances with heat lost from the surface of the heat-insulating layer to form a stationary temperature distribution.

The above-mentioned heat-generation of the fluid-transporting pipe can be considered as uniform all over the surface of the fluid-transporting pipe. Accordingly, if the heat-insulating layer is constructed uniformly, the surface temperature of the heat-insulating layer should become uniform provided that the heat loss from both the ends of the fluid-transporting pipe be neglected, but if the heat-insulating layer is not uniform, the effect of the heat-insulation is also not uniform, and the surface temperature does not show a uniform value and some variance should appear.

The surface temperature becomes usually higher than ambient atmospheric or room temperature by several degrees to ten odds degrees. If the variance of the heat-insulation effect becomes greater than 10 to 20%, the variance of the surface temperature will be as great as several degrees (°C).

The present invention, in short, lies in a method for finding the variance of the heat insulation effect by measuring the variance of the surface temperature. The variance of the surface temperature is usually calculated as variance or deviation from a standard temperature (which is often calculated as design value). In the method of the present invention the measurement of the surface temperature is not carried out by direct contact of a temperature sensor with the surface of a material the temperature of which is to be measured, but it is arranged that the total or a local surface of the heat-insulating layer is measured at a remote place by using a non-contact thermometer such as an irradiation thermometer which utilizes irradiation of infrared ray from the source of temperature.

In the foregoing part, description has been made for the case where the material of the fluid-transporting pipe is of an electrically conductive metal and heat generation is carried out by letting an induction current flow through the pipe, but if a metal pipe is laid along a fluid-transporting pipe, whether it is of an electrically conductive metal or an insulating material such as plastics, so long as it is situated in the inside of a heat-insulating layer and capable of conducting heat to the heat-insulating layer, it is possible to similarly inspect the heat-insulating layer surrounding the fluid-transporting pipe by inserting a conductor line in the metal pipe, holding it there, and generating induction heat.

An example in which such a metal pipe is worth installing separately from the fluid-transporting pipe, is a case where the metal pipe is of a heat-generating material for heating the fluid in the transporting pipe, particularly a case where the metal pipe is of a ferromagnetic material for constructing a skin effect current heat-generating pipe.

Figure 2:
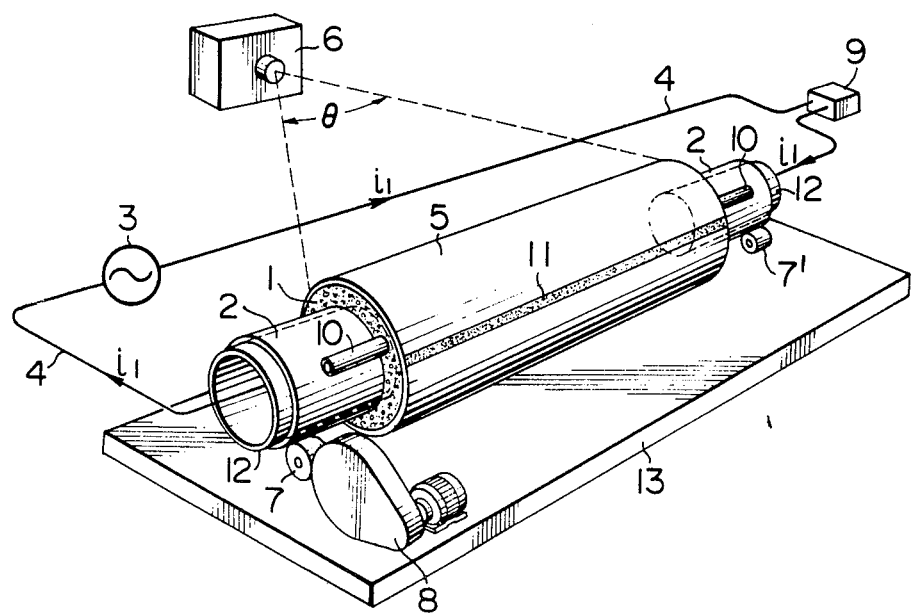
FIG. 2 is a perspective view of a system used in the method of the present invention for inspecting the performance of a heat-insulating layer surrounding a pipe according to the present invention.

Description will be further made referring to the accompanying drawings, FIGS. 1 and 2. In both the FIGS. 1 and 2, the symbols used represent the same things, but in FIG. 1 which shows the principle of a heat-generating circuit, the heat-insulating layer 1 shown in FIG. 2, the performance of which layer is to be inspected, is omitted.

In FIG. 1, numeral 2 is a fluid-transporting pipe (or an electrically conductive metal pipe laid along a fluid-transporting pipe) through which a secondary induction current $i_2$ is to flow, and is usually a steel pipe in most of the case. Numeral 3 is an AC source. Numeral 4 is a conductor line which forms a primary circuit, through which a primary current $i_1$ flows. The flanges 12 at both the ends are a tertiary heat-generating circuit for compensating heat loss from the ends of the transporting pipe 2, wherein an electric current $i_3$ flows and generates heat. It is possible to omit them if a standard temperature distribution in the direction of length of the transporting pipe is known in advance. If the flanges 12 satisfy the relations of the above formulas (1) and (2), the tertiary heat-generating current $i_3$ also becomes approximately equal to $i_1$ ($i_1 \approx i_3$). If $i_2$ and $i_3$ are uniformly distributed along the direction of circumference of pipes 2 and 12, respectively, heat generation per unit area of pipes 2 and 12 becomes uniform.

For letting current distribute uniformly, if the transporting pipe 2 and the flanges 12 are made of a ferromagnetic steel pipe, a conductor line 4 as a primary circuit can be inserted and held in any arbitrary point in the cross-section of the pipes. However, in the case where the pipes are non-ferromagnetic, it is preferable to insert in and hold at the central part of the pipes as straightly as possible.

FIG. 2 is a perspective view of the system for practicing the method of the present invention. The principle of the heat-generation has been already described referring to FIG. 1.

In FIG. 2, numeral 1 is a heat-insulating layer. When the temperature of fluid is higher than room temperature, it is a warmth-keeping material but when the temperature of the fluid is lower than room temperature, it is a coldness-keeping material. Numeral 5 is a cover for protecting the heat-insulating layer from outside harmful effect, moisture, etc. Numeral 6 is, for example, an infrared ray irradition type thermometer and the angle $\theta$ showing the measurement range must be sufficient to cover the whole length of the prefabricated heat-insulating layer to be inserted. Numerals 7 and 7' are rollers for rolling the prefabricated unit transporting pipe by way of a motor 8. Numeral 9 is a connector for connecting a conductor line 4. The primary current $i_1$ is usually in the order of 10 to several hundred amperes although it varies depending upon the diameter of transporting pipe 2, the thickness of heat-insulating layer, material, etc.

Figure 3:
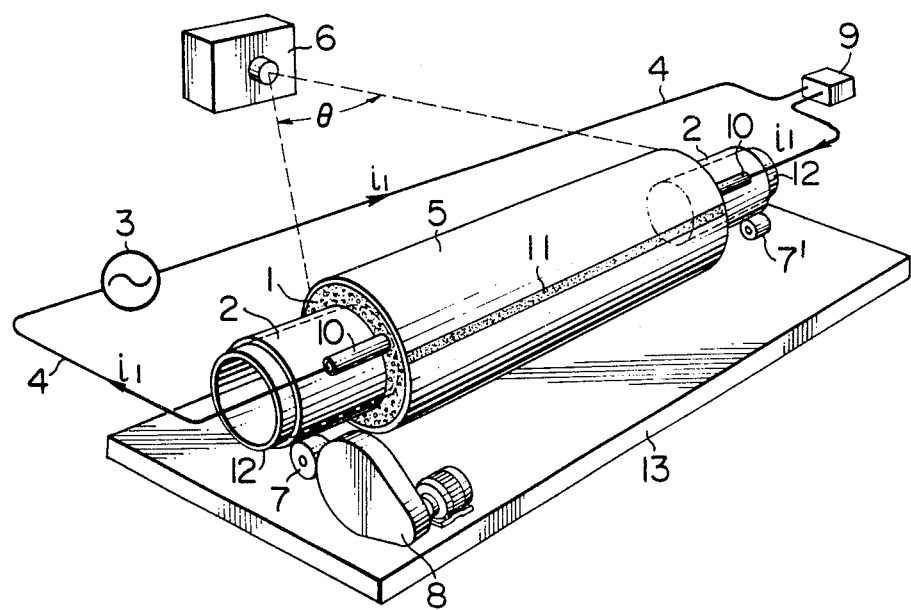
FIG. 3 is a perspective view of another system used in the method of the present invention for inspecting the performance of a heat-insulating layer surrounding a pipe according to the present invention.

Accordingly, the connector 9 must be of a kind which is simple for connecting in case of large current, and those useful for that purpose are commercially available lately. Numeral 10 is a ferromagnetic pipe such as steel pipe used for e.g. skin effect current heat-generating pipe (see Electrical Engineering Handbook (Japan), 1978 edition, page 1578). FIG. 3 shows that when a transporting pipe 2 is a non-magnetic pipe and holds a ferromagnetic pipe 10 and the electric source is of commercial frequency, this pipe 10 can also be used for induction heating by holding an insulated conductor line therethrough.

The numerals and symbols of FIG. 3 same as those of FIG. 2 have same meanings as those of numerals and symbols of FIG. 2.

Numeral 11 shows a part painted with a paint of high irradiation rate. This part becomes necessary when the cover 5 of the heat-insulating layer 5 has a low irradiation rate as in case of aluminum plate or zinc-plated steel plate and is difficult for use in the case of accurate temperature measurement. Numeral 13 is a supporting base for the whole.

In FIGS. 1, 2 and 3 an insulated conductor line 4 forming a primary circuit is a single line with one turn, but if the number of turns is n, the primary current $i_1$ becomes $i_1/n$ and the voltage of an electric source 3 will be n times. The voltage is in the range of about 2~5 V when the transporting pipe has a length of about 10 m in case of a single line with one turn, and one half of this voltage becomes the voltage which appears on the outer surface of the transporting pipe 2.

Accordingly, in order that $i_2$ does not flow from the outer surface of the transporting pipe 2 to an electric conductor contacting therewith, an arrangement for a suitable insulation becomes necessary. However, since the voltage appearing on the outer surface of the pipe 2 is so low as above-mentioned, and since the flanges 12 have a short length of pass for electric current, the voltage will be much lower; hence the insulation can be carried out in a simple practical manner.

In the method of the present invention, the temperature of a unit pipe in the above-mentioned construction is elevated and thereafter while the prefabricated unit pipe is rotated at a very small velocity by a motor 8, the surface temperature of the cover 5 of the heat-insulating layer 1 is measured by scanning over the whole surface of the cover by an irradiation thermometer 6. The time necessary for this measurement is usually within 5 minutes.

When a heat-generating source is a skin effect current heat-generating pipe 10, the whole revolution in one direction by way of the motor 8 is difficult; hence swinging may be preferable.

The time required for elevating the temperature of a unit pipe is usually longer than the above-mentioned time and sometimes amounts to several ten minutes; hence the preheating may be carried out by using a separate circuit as indicated in FIG. 1.

The time necessary for the method of the present invention may look longer, but since about several tens minutes to several hours are necessary for prefabricating the heat-insulating layer of the unit pipe, the time is only a slight increase in the necessary time, as a whole.

The irradiation thermometer shows a mean value relative to the surface area of the heat-insulating layer to an extent of area of square having a length of several centimeters on each side, though there is a slight difference depending upon the thickness of the heat-insulating layer and the distance between the thermometer and the heat-insulating layer. However, such value can be said to be sufficiently accurate for a pipeline having a usual heat-insulating layer.

Recently pipelines which require accurate temperature maintenance over a long distance are increasing in number. For example, for a pipeline for transporting molten sulfur, a lower limit of the temperature range is 120° C. and an upper limit is 150° C. The maintenance of these values over the length of several Km to several 10 Km of pipeline is important even at the time of transportation, and more important at the time of stoppage of transportations during which time temperature maintenance by heating is necessary. Thus the inspection of the performance of temperature maintenance of insulating material is necessary before shipping of prefabricated units. According to the present invention, the above-mentioned requirement can be fulfilled in economical, accurate and prompt way. Particularly it is to be noted that there is no need of setting terminals on the side of a pipe having a heat-insulating layer according to the inspection method of the present invention, because it utilizes heating by induction current.

What is claimed is:

1. A method of inspecting the heat-insulation performance of a heat-insulating layer surrounding the outer wall of a metal pipe, which method comprises
   (a) inserting an insulated electrical conductor line through the interior of said metal pipe and maintaining it in said pipe during the time of inspection;
   (b) flowing an AC current through said conductor line to thereby induce a secondary induction current in said metal pipe,
      (1) said metal pipe having a wall thickness greater than twice the skin depth of the AC current induced therein and flowing therethrough to produce a substantially constant heat generation per unit surface area in said metal pipe,
   (c) waiting until the secondary induction current in said metal pipe has caused the outer surface of said heat insulating layer to increase in temperature, and
   (d) measuring the temperature of at least a portion of the outer surface area of said heat-insulating layer by means of a non-contact thermometer to thereby ascertain whether there is any variable in the measured temperature over the outer surface of said heat-insulating layer due to non-uniformity in the heat-insulating performance of said heat insulating layer.

2. A method according to claim 1 wherein heat loss from the pipe is compensated at the time of heating by providing a tertiary heating circuit.

3. A method according to claim 1 wherein said metal pipe having a heat-insulating layer therearound is rotated or swung at the time of the temperature measurement.

4. A method according to claim 1 wherein a ferromagnetic pipe is used as said metal pipe.

5. A method of inspecting the heat-insulation performance of a heat-insulating layer surrounding the outer wall of a pipe along which a metal pipe is laid and situated in the interior of said insulating layer, which method comprises
   (a) inserting an insulated electrical conductor line into the interior of said metal pipe and maintaining it in said metal pipe during the time of inspection,
   (b) flowing an AC current through said conductor line to thereby induce a secondary induction current in said metal pipe,
      (1) said metal pipe having a wall thickness greater than twice the skin depth of the AC current induced therein and flowing therethrough to produce a substantially constant heat generation per unit surface area in said metal pipe,
   (c) waiting until said secondary induction current in said metal pipe has caused the outer surface of said heat insulating layer to increase in temperature,
   (d) measuring the temperature of at least a portion of the outer surface area of said heat-insulating layer by means of a non-contact thermometer to thereby ascertain whether there is any variance in the measured temperature over the outer surface of said heat-insulating layer due to non-uniformity in the heat-insulating performance of said heat-insulating layer.

6. A method according to claim 5 wherein said pipe having a heat-insulating layer therearound is rotated or swung at the time of the temperature measurement.

7. A method according to claim 5 wherein a ferromagnetic pipe is used as said metal pipe.

* * * * *